United States Patent [19]

Balkin

[11] Patent Number: 5,656,284
[45] Date of Patent: Aug. 12, 1997

[54] ORAL TRANSMUCOSAL DELIVERY TABLET AND METHOD OF MAKING IT

[76] Inventor: Michael S. Balkin, 191 E. Main St., Huntington, N.Y. 11743

[21] Appl. No.: 427,439

[22] Filed: Apr. 24, 1995

[51] Int. Cl.$^6$ ..................................................... A61K 9/20
[52] U.S. Cl. ........................... 424/435; 424/465; 514/777
[58] Field of Search ................................... 424/435, 465; 514/777

[56] References Cited

U.S. PATENT DOCUMENTS

| | | |
|---|---|---|
| 4,597,959 | 7/1986 | Barr . |
| 4,829,056 | 5/1989 | Sugden . |
| 4,842,854 | 6/1989 | Babaian et al. ........................ 424/435 |
| 4,915,948 | 4/1990 | Gallopo et al. . |
| 4,948,580 | 8/1990 | Browning . |
| 4,994,276 | 2/1991 | Baichwal et al. . |
| 5,053,032 | 10/1991 | Barclay et al. ........................ 604/892.1 |
| 5,069,906 | 12/1991 | Cohen et al. ........................... 424/430 |
| 5,077,051 | 12/1991 | Gallopo et al. . |
| 5,128,143 | 7/1992 | Baichwal et al. . |
| 5,231,090 | 7/1993 | Hsia et al. ............................. 424/449 |
| 5,330,761 | 7/1994 | Baichwal ................................ 424/469 |

OTHER PUBLICATIONS de Vries, M.E., Bodde, H.E., Verhoef, J.C., Junginger, H.E., "Developments in Buccal Drug Delivery," *Critical Reviews in Therapeutic Drug Delivery Systems*, CRC Press, Inc., 1991, 8(3), pp. 271–303.

Merkle, H.P., Anders, R., Sandow, J., Schurr, W., "Drug Delivery of Peptides: The Buccal Route," *Delivery Systems for Peptine Drugs*, 1986, pp. 159–175.

Cassidy, J. et al., "Human Transbuccal Absorption of Diclofenac Sodium from a Prototype Hydrogel Delivery Device," *Pharmaceutical Research*, vol. 10, No. 1, 1993, pp. 126–129.

Arnott, S., Fulmer, A., Scott, W.E., Dea, I.C., Moorhouse, R., Rees, D.A., "The agarose double helix and its function in agarose gel structure," *J. Mol Biol.*, 1974, pp. 269–284.

Wolf, G., Casper, R. J., "Disc electrophoretic separation of elongated plant viruses in polyacrylam," *Gen. Virol.* 1979, 12: pp. 325–329.

Geller, J. et al., "Therapeutic Controversies: Clinical Treatment of Benign Prostatic Hyperplasia," *Journal of Cinical Endocrinology & Metabolism*, vol. 80, No. 3, pp. 745–756.

Balkin, M. S., Sonenberg, M., "Hormone–induced homologous and heterologous desensitization in the rat adipocyte," *Endocrinology*, vol. 109, No. 4, Oct. 1981, pp. 1176–1183.

Snyder, P.J., Utiger, R.D., "Response to thyrotropin releasing hormone (TRH) in normal man," *J. Clin Endocrinol Metab.* 1972, vol. 34, pp. 380–385.

Roorda, W.E., Bodde, H.E., De Boer, A.G. and Junginger, H.E., "Synthetic hydrogels as drug delivery systems," *Pharmaceutisch Weekblad Scientific Edition*, vol. 8, 1986, pp. 165–189.

Guiseley, K.B., Renn, D.W., "Agarose: Purification, Properties, and Biomedical Applications," *Marine Colloids Division, FMC Corporation*, 1975, pp. 1–23.

de Vries, M.E., Bodde, H.E., Verhoef, J.C., Junginger, H.E., "Developments in buccal drug delivery," *Crit. Rev. Ther. Drug Carrier Syst.*, 1991; Abstract.

de Vries, M.E., Bodde, H.E., Busscher, H.J., Junginger, H.E., "Hydrogels for buccal drug delivery: properties relevant for muco–adhesion," *J. Biomed Mater Res.*, Nov. 1988, Abstract.

Cassidy, J., Berner, B., Chan, K., John, V., Toon, S., Holt, B., Rowland, M., "Human transbuccal absorption of diclofenac sodium from a prototype hydrogel delivery device," *Pharm Re.*, Jan. 1993, Abstract.

Article entitled "Transmucosal patches: a new alternative.", pp. 5–6.

Balkin, M. et al., "Heterologous Desensitization in Acromegaly," First International Congress on Cancer and Hormones, Rome, Apr. 23–27, 1986, Abstract.

*Primary Examiner*—Carlos Azpuru
*Attorney, Agent, or Firm*—Baker & McKenzie

[57] ABSTRACT

A tablet for delivering a pharmaceutical to a human transmucosally is described. The excipient is a gel which is elastic enough for a comfortable fit in the mouth, has suitable gel strength, holds a suitable amount of pharmaceutical and has a structure which allows at least bi-directional delivery of the pharmaceutical to opposed oral mucosa. The tablet is placed between the upper lip mucosa and the opposite gingiva mucosa, and is held in place without any adhesive, by virtue of a snug fit and the elasticity of the tablet. The tablet is made from an organic polymer, e.g., agarose, and water, glycerol and a pharmaceutical, which may be any of a wide range of pharmaceuticals.

30 Claims, No Drawings

ORAL TRANSMUCOSAL DELIVERY TABLET AND METHOD OF MAKING IT

BACKGROUND OF THE INVENTION

The invention disclosed herein relates to a tablet for delivering a pharmaceutical to a human transmucosally, particularly to such a tablet which fits between opposed oral mucosa in the lip and gingiva, to a method for administering the tablet and to a method for making the tablet. "Pharmaceutical" is used herein in a broad sense, and includes drugs, medications, etc.; where the context permits, these words are used interchangeably herein.

Considerable attention has been focused in recent years on the delivery through the oral mucosa of drugs which have a high first pass metabolism (i.e., metabolized to a large extent by the liver during the first pass therethrough and therefore do not enter the blood stream) or degrade in the gastrointestinal tract. Transmucosal delivery has also been considered for treatment of oral disorders and as a local anesthetic. See for example: *Developments in Buccal Drug Delivery*, M. E. de Vries et al., published in *Critical Reviews in Therapeutic Drug Delivery Systems*, 8(3), pp 271–303, CRC Press, Inc., 1991; *Drug Delivery of Peptides: The Buccal Route*, H. P. Merkle et al., published in *Delivery Systems for Peptine Drugs*, E. Tumlinson and S. S. Davis, editors, pp. 159–175, Pleunum Press, 1986; *Human Transbuccal Absorption of Diclofenac Sodium from a Prototype Hydrogel Delivery Device*, J. Cassidy et al., published in *Pharmaceutical Research*, Vol. 10, No. 1, 1993, pp. 126–129; and a recent announcement by 3M of a transmucosal patch. There are a number of major advantages to delivering pharmaceuticals transmucosally in a buccal tablet as opposed to oral delivery in a conventional pill which is swallowed. Some of these advantages are recognized by the pharmaceutical industry and/or physicians, and others may not be. Those that are believed to be recognized by others are described immediately below, and those that are not are described further below. Also, although a particular advantage of the buccal administration of drugs may be known, the application of that advantage to a particular pharmaceutical or class of pharmaceuticals may not be known.

Two advantages of buccal administration are currently recognized commercially or in the medical literature. The first known advantage is rapidity of action. Medications administered bucally enter the blood stream immediately after passage through the buccal mucosa instead of first having to be swallowed and then having to pass through a portion of the gastrointestinal tract before being absorbed. This rapidity of action is one of the reasons that one commercially available and one experimental product for pain relief have been administered via the buccal route. The first of these products contains nitroglyerin, and is available as a buccal pill that adheres to the mucosa, sold under the trademark Nitrogard. The second product contains the non-steroidal anti-inflammatory analgesic diclofenac which has been used in an experimental buccal pill that adheres to the mucosa (see previous reference by J. Cassidy). The second known advantage of the buccal route is to allow administration of medications which cannot normally be administered orally. Additional unique advantages of the buccal route and the medications that exploit these advantages are described below, as well as additional medications that could be administered buccally to exploit the two previously mentioned advantages of the buccal route.

The buccal tablets and patches described so far were adhered to the cheek or the gum, and provided for direct delivery of the pharmaceutical carried by the tablet or patch through only a single mucosa, either the mucosa to which the tablet or patch was adhered or the mucosa opposite thereto. Buccal tablets and patches, which must remain in the mouth for a particular length of time in order to transmucosally deliver a therapeutically effective amount of the pharmaceutical, suffer from the competing constraints that they contain a relatively large amount of the pharmaceutical and yet be small enough stay in the mouth for hours at a time with minimum discomfort, and without moving and risk of being swallowed. Additionally, the tablet or patch should be maintained in direct contact with a mucosa to reduce the effects of salivary washout of the pharmaceutical. To that end, the tablets and patches described so far, as mentioned, all have been adhered in the mouth to positively hold them in place adjacent an oral mucosa over long periods of time. The use of an adhesive imposes five limitations on a buccal tablet or patch. First, the adhesive, e.g., a hydrogel self-adhesive, with which such tablets are adhered in the mouth may inflame or damage the buccal mucosa over prolonged use. Even though such damage may not result in health problems in the mouth, it may interfere with absorption of a pharmaceutical particularly with prolonged use. Secondly, the use of an adhesive limits absorption to only one mucosal surface, the one to which the adhesive is attached. Thirdly, the adhesive, unless it is permeable, reduces the amount of surface area available for drug absorption across the one mucosal surface in contact with the buccal tablet. Fourthly, the use of an adhesive adds to the complexity and expense of fabricating a buccal tablet. Fifthly, the use of an adhesive system reduces the volume of the buccal tablet that can be devoted to containing the drug and thus reduces its drug capacity.

There is therefore a need for devices that will deliver a therapeutically-effective amount of a pharmaceutical transmucosally which have one and preferably more of the following characteristics: are relatively small; contain a relatively large amount of the pharmaceutical; may remain in the mouth for long periods of time without moving and with little or no discomfort and without damaging the buccal mucosa, can deliver the pharmaceutical relatively quickly; can sustain delivery of therapeutically effective levels of a pharmaceutical over time; can allow a greater amount of mucosal surface to be used for absorption than previously described buccal tablets or patches; and is simple and inexpensive to fabricate.

SUMMARY OF THE INVENTION

It is an object of the invention disclosed herein to provide a tablet which has one or more of the characteristics described above.

It is another object of the invention to provide such a tablet which may be maintained in place in the mouth without a separate adhesive or a self-adhesive.

It is another object of the invention to provide such a tablet that may be maintained in the mouth at a location sheltered from large amounts of saliva.

It is another object of the invention to provide a more comfortable and yet therapeutically effective method of delivering a pharmaceutical to a human transmucosally.

It is another object of the invention to utilize the mucosa of the lip and the opposed gingiva, particularly the mucosa of the upper lip and the opposed gingiva, to transmucosally deliver a pharmaceutical, and to provide a tablet sized to fit snugly and relatively comfortably therebetween.

It is another object of the invention to provide for buccal delivery of pharmaceuticals not heretofore recognized or identified as being advantageous to be delivered, or deliverable at all, buccally.

It is another object of the invention to provide a tablet for use in delivering a pharmaceutical transmucosally that releases the pharmaceutical in at least two different directions, e.g., in opposite directions.

It is another object of the invention to provide a method of making the tablets described herein.

The invention achieves the above and other objects by providing the tablets described herein, a method for delivering pharmaceuticals employing the tablets and a method for making the tablets.

Tablets embodying the invention contain a pharmaceutical and an excipient, and are sized to be held in the mouth between a lip mucosa and a gingiva mucosa; have a structure which releases the pharmaceutical multi-directionally, e.g., at least bi-directionally in generally opposite directions to both of the opposed lip mucosa and gingiva mucosa; and hold a quantity of a wide range of pharmaceuticals sufficient to provide a therapeutically effective dose within a given time. Multi-directional release from a tablet simply means that the pharmaceutical contained in the tablet exits the tablet from more than one side or surface of the tablet, and for a substantially two-sided tablet, the pharmaceutical would exit substantially bi-directionally in generally opposite directions. Preferably, a tablet embodying the invention placed between the lip mucosa and the opposed gingiva mucosa remains there solely by virtue of its size and the fit, and does not require a separate adhesive or a self-adhesive to there it in the mouth, which simplifies tablet manufacture, facilitates at least bi-directional delivery of the pharmaceutical held in the tablet to the opposed mucosa between which the tablet is held, and reduces discomfort. Bi-directional delivery to opposed mucosa of course increases the speed of delivery as compared with delivery of the pharmaceutical to a single mucosa (assuming mucosa of comparable size and absorption characteristics). The small size of the tablet enables it to comfortably remain between a lip mucosa and a gingiva mucosa for long periods of time without being adhered and without substantial movement and risk of swallowing, while in contact with the mucosa and sheltered from contact with large mounts of saliva present elsewhere in the mouth.

In a preferred embodiment, the tablet is sized to fit and remain, without being adhered, between opposed mucosa in the upper lip and the upper gingiva opposed thereto. Also, in the preferred embodiment of the tablet, the excipient holding the pharmaceutical is one which is insoluble in saliva, holds a suitable amount of pharmaceutical and has a structure which allows at least bi-directional, and preferably multi-directional, delivery of the pharmaceutical. Further, in the preferred embodiment, the tablet is elastic, and the excipient holding the tablet is an elastic gel. The elasticity of the tablet contributes to holding it in place between the opposed lip and gingiva mucosa without an adhesive. Suitable gels are those which are elastic enough for a comfortable fit, have suitable gel strength, and also hold suitable amount of pharmaceutical and have a structure which allows at least bi-directional delivery of the pharmaceutical.

The preferred gels are produced from organic polymers that have the following properties. They can be dissolved in aqueous solutions with mild healing and mixing. As the solution of these polymers cools, strong gels are formed even at very dilute concentrations. The resulting gels have very large pores allowing unhindered movement of non-polymer molecules within them. The gels exhibit considerable hysteresis, that is the melting point of the gels occurs at a significantly higher temperature than the setting temperature and this melting temperature is significantly higher than the normal human body temperature of 37° C. Among the preferred organic polymers to form these gels are those from the following groups: agarose, agar, agar derivatives, carrageenans, algin, furcellaran, pectins, xanthan gum and locust bean gum, with agarose being the presently preferred organic polymer. Other organic polymers which form gels that satisfy the criteria described herein may also be used.

The tablet also preferably includes glycerol which improves elasticity and tensile strength. In addition, the use of glycerol enhances the solubility of many substances in solution, thus allowing the tablet to contain increased concentrations of pharmaceuticals. Preferably the tablet has a modulus of elasticity of from about $5 \times 10^4$ to about $5 \times 10^7$ dyne/cm$^2$ and a tensile strength requiring a force of from about 600 to about 2000 g/cm$^2$ to be applied before the gel will rupture as measured by the Marine Colloids' Gel Tester.

Tablets are prepared in a solution with polymer concentrations (w/w) ranging from 0.1% to 10%, excluding the pharmaceutical, and with glycerol concentrations (w/w) ranging from 0% to 75% excluding the pharmaceutical. The amount of a pharmaceutical in the tablet depends principally on its solubility and can comprise up to 50% of the weight of the tablet.

For agarose and carregeenan the presumed gelling mechanism, determined from evaluation of X-ray diffraction data, is through the formation of double helix structures at junction points between individual polymers. (See The agarose double helix and its function in agarose gel structure; Arnott S., Fulmer A., Scott W. E., Dea I. C., Moorhouse R., Rees D. A., *J Mol Biol* 1974 Dec. 5; 90 (2):269–84.) The resulting gel structures have extremely large pores which, based on the use of agarose for electrophoresis and gel filtration, can be assumed to allow free passage in any direction of molecules and particles even as large as plant viruses. (Disc electrophoretic separation of elongated plant viruses in polyacrylam; Wolf G. & Casper R. J., Gen. Virol 1979; 12:325–29.) Thus in addition to pharmaceutical molecules, liposomes can be transported in the tablet to the mucosal surface. Entirely surrounded by buccal mucosa that has a very high blood flow rate (2.4 ml/min/cm$^2$ in the Rhesus monkey; *Developments in Buccal Delivery*, referenced above) the tablet allows the rapid transport in all directions of pharmaceutical down its concentration gradient and across the buccal mucosa.

A method embodying the invention for delivering a pharmaceutical transmucosally to a human, comprises providing a tablet as described above, placing the tablet in the mouth between the lip mucosa and gingiva mucosa, and allowing it to remain there for a time sufficient to deliver a therapeutically effective amount of the pharmaceutical to the human. As mentioned above, the tablet is preferably sized to fit and remain, without adhering, between opposed mucosa in the upper lip and the upper gingiva opposed thereto, and the step of placing the tablet in the mouth comprises placing it between the opposed upper lip and upper gingiva mucosa.

A method embodying the invention for making a gel carrying a pharmaceutical, comprises mixing water and the organic polymer in proportions sufficient to form a colloidal gel, and mixing a pharmaceutical therewith before the water and organic polymer have gelled; and subjecting the resulting mixture to conditions which cause the mixture to gel.

The mixing step may comprise mixing the water and the organic polymer separate from the pharmaceutical, and then mixing the pharmaceutical into the mixture obtained from the water and the organic polymer, or adding the water, the organic polymer and the pharmaceutical all together and mixing them together. The mixing step preferably comprises also mixing glycerol before the water and the organic polymer are able to gel. The glycerol may be mixed with the organic polymer and water before or after the pharmaceutical is added, or all ingredients may be mixed together.

Unlike a conventional hydrogel tablet which requires an impermeable backing to prevent loss of pharmaceutical into the oral cavity (and also usually requires the separate incorporation of the pharmaceutical into the gel after it is formed) and must therefore be fabricated in multiple steps, a tablet made according to the invention can be manufactured in a single step in which all the ingredients are combined and form a finished product as gelling occurs. Thus, the method for forming the tablet is greatly simplified, and does not require time-separated steps for first forming the gel and then incorporating the pharmaceutical.

The tablet may hold any of a wide range of pharmaceuticals that are compatible with oral delivery and which may be held by a gel, including but not limited to those described herein. Use of the inventive buccal tablet or a prior art buccal tablet to deliver some of the pharmaceuticals described below may be novel.

As discussed above, buccal tablets have the two currently known advantages of rapidity of action and allowing the administration of medications which can not be administered orally. Six additional advantages, which are not known to the applicant to be currently recognized commercially or in the medical literature, are described further below. The first two advantages, which are rapidity of action and the ability to administer drugs destroyed if ingested orally, have already been exploited commercially in the form of a nitroglycerin buccal patch.

As far as the first advantage, rapidity of action, is concerned several classes of medications would have improved efficacy if administered via the buccal route. One class of medications for which rapidity of action is important and which could be placed in buccal tablets in general and the inventive buccal tablet in particular are analgesics which include aspirin, ibuprofen, fenoprofen, sulindac, salsalate, diflunisal, mecleofenamate, naproxen, nabumetone, tolmetin, diclofenac, oxaprozin, indomethacin ketoprofen, choline salicylate, piroxicam, mefenamic acid, etodolac and ketorolac. Another class of medications where rapidity of action is important and which could be incorporated in the inventive tablet are antiarrhythmic agents including adenosine, atropine, bretylium, disopyramide, flecainide, metoprolol, mexiletine, moricizine, procainamide, propafenone, propanolol, quinidine, sotalol, tocainide, quinidine and verapamil.

As far as the second advantage of buccal administration, the ability to administer drugs that cannot be ingested because of drug destruction, there are several drugs which are potentially in this category. Testosterone could be placed in a buccal tablet and could then be administered via the oral route to avoid destruction via first pass metabolism. Normally such metabolism necessitates the administration of testosterone via injection or a large skin patch worn on the scrotum. However, the scrotal patch has an important potential disadvantage since scrotal skin generates an increased amount of a testosterone metabolite, 5 alpha-dihydrotestosterone, that can potentially stimulate prostate hypertrophy (see, for example: *Therapeutic Controversies: Clinical Treatment of Benign Prostatic Hyperplasia*, J. Geller et al., published in *Journal of Clinical Endocrinology & Metabolism*, Vol. 80, No. 3, p. 745). Other medications which could be incorporated in a buccal table and which normally are destroyed by hepatic first pass metabolism and must therefore be otherwise administered via injection include the anti-migraine medication sumatriptan and the antiarrhthmic lidocaine.

Six additional advantages of the buccal route in general, and for which buccal tablets in general and the buccal tablet described herein in particular are well suited are described below.

The first of these advantages is that buccal administration would greatly reduce the effect of a drug on non-drug related liver metabolism compared to its administration in oral form. A medication given buccally is equally distributed to most of the body, as opposed to oral administration which results in the liver being first exposed to virtually all the administered drug. Estrogen is an example of a drug that could potentially be delivered with increased efficacy if administered buccally. Currently postmenopausal women who are candidates for estrogen replacement receive less than a full replacement dose of estrogen mainly to avoid estrogen side-effects including its property of inducing liver production of clotting factors which in turn can lead to phlebitis and even pulmonary emboli. By administering estrogen buccally there would be a decreased exposure of the liver to estrogen and less induction of clotting factors. Thus, postmenopausal women could be given a higher dose of estrogen via the buccal route which might result in potentially beneficial effects on the skeletal and cardiovascular systems which are adversely affected by low estrogen states.

Similarly, many drugs affect liver metabolism of other drugs. This affect would be greatly attenuated by administering such drugs in buccal form. One class of drugs in this category are medications that inhibit metabolizing enzymes in the liver resulting in increased concentrations of other drugs. Another class of drugs increases metabolizing enzymes in the liver resulting in decreased concentrations of other drugs. By administering both classes of these drugs using a buccal tablet there would be less effect on the concentration of other drugs and thus the avoidance of toxic as well as subtherapeutic drug levels. Drugs in the category of liver enzyme inhibitors which could be administered via a buccal tablet include allopurinol, ketoconazole, cimetidine, metronidazole, ciprofloxacin, diltiazem, fluconazole, propoxyphene, verapamil, itraconazole, erthyomycin, quinidine, omeprazole, micronazole and monamine oxidase inhibitors such as isocarboxazid and phenelzine. Drugs in the category of liver enzyme inducers which could be administered via a buccal tablet include cabamazepine, phenytoin, glutethimide, primidone, rifampin and barbiturates such as phenobarbital, pentobarbital, secobarbital, amobarbital and butabarbital.

The second of these advantages is that buccal administration would reduce the exposure of the liver to drugs that are potentially hepatotoxic. In the event an individual had suffered a previous toxic liver reaction after ingestion of one of these medications, administration via a buccal tablet might allow such a patient the opportunity to use the previously toxic medications. Drugs that are potentially hepatotoxic and which could be administered buccally include phenothiazines such as chlorpromazine, fluphenazine, prochlorperazine, promazine, promethazine, thioridazine and triflupromazine; also other antipsychotic drugs such as chlorprothixene and haloperidol; also benzodiazepines such as diazepam, chlordiazepoxide and oxazepam; also the monamine oxidase inhibitors previously mentioned; also tricyclic antidepressants such as amitryptiline, desipramine, doxepin, imipramine, nortriptyline and protriptyline; also anticonvulsants such as phenacemide, trimethadione, mephenytoin, paramethadione, phenytoin, phenobarbital and cabamazepine; also the analgesic agents previously mentioned including acetaminophen, allopurinal, diclofenac and indomethacin; also hormonal agents including anabolic steroids, oral contraceptives, tamoxifen, danazol and glucocortiocides; also oral hypoglycemics such as acetohexamide, chlorpropamide, tolbutamide and tolazemide; also the antithyroid drugs carbimzole, methimizole and propylthiouracil; also antimicrobials such as rifampicin, sulfonamides, sulfones, nitrofurantoin, para-aminosalicylic acid, griseofulvin, ketcochazole, flursosine, vidarabine; also cardiovascular drugs such as amiodarone, captopril, disopyramide, furosemide, hydralazine, methyldopa, nicotinic acid, nifedipine, procainamide, quinidine and verapamil; also miscellaneous drugs including vitamin A, ranitidine, cimetidine, levodopa and isotretinoin. A specific combination of drugs associated with liver toxicity consists of the anticonvulsant phenytoin in combination with either chloramphenicol, or disulfiram or isoniazid; another combination of drugs which can cause liver toxicity consists of the anticonvulsant carbasmazepine in combination with either propoxyphene, or erythromycin, or isoniazid. Placing one of the pair of these potentially toxic combinations in a buccal tablet can then allow the combination to be administered more safely.

The third of these advantages of buccal administration is that it results in much less exposure of the GI tract to a drug as opposed to oral ingestions. One of the side effects of many antibiotics is the destruction of normal GI flora resulting in diarrhea and overgrowth with dangerous organisms such as *C. difficile*. Antibiotics that could be incorporated in a buccal tablet, which would then have enhanced safety because of reduction in the toxic effect on gut flora, include cephlosporins such as cephalexin, cefadroxil, cefaclor, cefamandone, cefuroxime, cefprozil, cefpodoxime, loracarbef and cefixime; also penicillins including penicillin G, penicillin V, cloxacillin, dicloxacillin, nafcillin, oxacillin, ampicillin, carbenecillin, amoxicillin alone and amoxicillin in combination with potassium clavulanate; also macrolide and related compounds including erythromycin, azithromycin, clarithromycin, troleandomycin, clindamycin and lincomycin.

The fourth of these advantages of buccal administration is that it allows drugs to be administered which would otherwise interfere with the absorption of other drugs. In particular iron supplements can be administered via a buccal tablet with the avoidance of many adverse effects on the absorption of other medications such as thyroid hormone.

The fifth of these advantages of buccal administration is that it increases the practicality of administering drugs whose absorption is adversely affected by the presence of food. Tetracyclines, in particular, could be administered buccally thus avoiding the effects of food on tetracycline administration which otherwise complicates the administration of this class of antibiotics via the oral route.

The sixth of these advantages of buccal administration is that it allows blood lipids such as cholesterol to be lowered and modified in ways not possible through the oral ingestion of medications. Lipids can be incorporated into a buccal tablet. Lipids absorbed via the buccal mucosa bypass liver metabolism and can directly interact with endogenous lipoproteins thus influencing blood lipid levels. Recently an acute lowering of cholesterol has been demonstrated by applying lecithin to the skin (U.S. Pat. No. 5,231,090). Such an impractical method could be replaced by administering lecithin via the buccal route.

DESCRIPTION OF THE PREFERRED EMBODIMENTS

The invention encompasses tablets made from gels which satisfy the criteria described herein. As currently preferred, the gel comprises water, agarose powder and glycerol. The invention will be described in more detail below in the context of the preferred embodiments thereof. However, it should be understood that the invention is not limited to the specific details of the preferred embodiments described below.

The tablet is preferably sized to fit between the upper lip and the upper gingiva opposite thereto without being adhered. The tablet may have any suitable shape. For example, an elliptical or disc shape with a substantially two-sided configuration, or a round shape is preferred. An elliptical or disc-like tablet would have two major sides, and either no minor sides or small minor sides in comparison to the major sides. In such a tablet, the pharmaceutical would exit substantially bi-directionally. The preferred maximum diameter of an elliptical, disc-like or round tablet can range from 0.2 cm to 2.0 cm and the thickness can vary from 0.1 cm to 1.0 cm, although the exact maximum diameter and thickness may vary and are not precisely critical.

The tablet comprises the preferred hydrogel such as agarose at a concentration (w/w) that can range (excluding the pharmaceutical) from 0.1% to 10%, a more preferred concentration of 0.3% to 3% and a most preferred concentration of 1.5%. The tablet also can include glycerol at a concentration (w/w) that can range (excluding the pharmaceutical) from 5% to 75%, a more preferred concentration of from 10% to 60% and a most preferred concentration of 25%. However, it need not contain glycerol. The tablet also contains a pharmaceutical whose maximum concentration is limited principally by its solubility in an aqueous or an aqueous and glycerol solution, e.g., TRH (thyrotropin releasing hromone) was successfully incorporated into the tablet at a concentration 0.55 molar and comprised 20% by weight of the tablet.

The tablet may carry any of a wide range of pharmaceuticals consistent with oral delivery and which may be held by a gel, as described above.

The tablet may be made as follows. The organic polymer and water are mixed, and a pharmaceutical is also mixed, before, during or after mixing the organic polymer and water but before gelling occurs. Preferably the pharmaceutical is mixed after the organic polymer and water are mixed, but the preferred sequence may depend upon the particular organic polymer and pharmaceutical. Glycerol is preferably also mixed, at any time before gelling, but preferably with mixing of the organic polymer and water. Again, the preferred sequence may depend upon the particular organic polymer and pharmaceutical. After gelling, the tablets are suitably packaged to prevent water loss.

According to the preferred embodiment which employs agarose as the organic polymer, agarose, glycerol and half the water to be used are placed in a beaker and brought into solution by heating to from about 71° C. to about 100° C. with continuous stirring. The solution is then added 1:1 to a previously prepared aqueous solution of a pharmaceutical. The mixture is vortexed and then quickly introduced into molds where gelling occurs as the temperature falls. Agarose gels at 36° C. and therefore the agarose solution, including the pharmaceutical, are kept above this temperature until introduced into the molds. A firm, useable tablet forms at room temperature within one hour. For temperature sensitive pharmaceuticals, the agarose solution, preferably prepared in a water bath, is allowed to cool to close to the gelling temperature before combining with the aqueous pharmaceutical solution. For those pharmaceuticals whose solubility improves with glycerol, the pharmaceutical can be solubilized in glycerated water rather than water alone. Pharmaceuticals which are relatively temperature insensitive can be added directly to the initial agarose solution before it is put into solution. This approach allows up to a doubling of the maximum pharmaceutical concentration in the tablet.

Liposomes can be incorporated into the tablet by adding agarose in solution to a solution of liposomes as the pharmaceutical solution, and then gently vortexing to prevent damage to the liposomes before introduction into molds where gelling occurs.

Tablets made from agarose undergo syneresis which is a slow tightening of the gel matrix with exudation of water. After an initial surge, which occurs during the first hour after gellation, this process slows and further water loss can be prevented by wrapping the tablets in foil or coating them with wax. The foil or wax is then removed prior to use. A simple way of removing the wax from the tablet is to wrap a tear string around the tablet prior to applying the wax. Pulling on the string then breaks the wax and allows the tablet to be removed.

The tablets may also comprise a syneresis-free gel. For example, the gel may be made from iota carrageenan which is syneresis-free and thus will not lose water in the gel state. In addition, the gel may be made from iota carrageenan combined with other carrageenans such as kappa carrageenans as well as agarose to produce syneresis-free gels.

The preferred agarose has the trade name SeaKem® (Marine Colloids, Division of FMC). For very temperature sensitive drugs an agarose that gels at a lower temperature can be used such as SeaPlaque® (Marine Colloids, Division of FMC).

As described above, the pharmaceutical is delivered from the tablet simply by placing the tablet between the upper lip and the opposite gingiva, and allowing it to remain there for a time sufficient for the lip and gingiva mucosa to absorb a therapeutically effective amount of the pharmaceutical.

A specific example of tablets made in accordance with the invention is described below, and a specific example of administering a pharmaceutical carried by the tablet is described below. Such examples are intended to be exemplary, and not exhaustive or limiting.

EXAMPLE 10 ml of water, 10 ml of glycerol and 600 mg of SeaKem® agarose (Marine Colloids, Division of FMC) were combined in a 40 cc beaker. The mixture was then brought into a colloidal solution by placing the beaker in a water bath at 100° C. while mixing continuously with a magnetic stir bar for ten minutes. Five cc's of gel were removed, placed in a plastic test tube that contained a thermometer, and was allowed to cool to 50° C. At that point 1.3 cc was pipetted into another plastic test tube that contained 1.3 cc of a 1.1 molar (400 mg/ml) solution of thryrotropin releasing hormone (TRH) in water. The mixture was vortexed and 0.2 cc aliquots were placed in tablet molds and allowed to gel at room temperature. A total of 10 tablets was made, each containing 40 mg of TRH.

Tablets made in accordance with the above example were used in a human study, the data from which was presented at the First International Congress on Cancer and Hormones, Apr. 23–27, 1986, Rome, Italy and published as an abstract in the Congress's Proceedings. In this study a patient with acromegaly was treated successfully with these tablets to induce heterologous desensitization, and thus decrease his excess secretion of growth hormone. (See: Hormone-induced homologous and heterologous desensitization in the rat adipocyte; Balkin M. S., Sonenberg M.; published in Endocrinology 1981 October 109(4).)

The following background is of value in understanding this study. Growth hormone (GH) is produced by the pituitary gland. Acromegalics are individuals with an excess of GH, usually due to a tumor of the pituitary gland. The hormone TRH when administered intravenously (iv) to both normal individuals and acromegalics stimulates the release of TSH and prolactin (Prl) from the pituitary gland. The thryoid hormone triiodothionine (T3), which is stimulated by TSH, also occasionally rises after intravenous TRH. TRH normally has no effect on GH except in acromegalics, a substantial portion of whom demonstrate an anomalous release of GH in response to TRH.

In this study a 28 year old man with active acomegaly, in whom the release of GH in response to iv TRH had been previously demonstrated, placed one of the TRH containing tablets described above in his mouth, between the upper lip and upper gingiva, for three hours, twice a day for a period of five days. The response of GH and Prl in ng/ml, TSH in mIU/ml and T3 in ng/dl to the first and last of these tablets was measured in blood samples drawn over 180 minutes. The results are presented in tabular form below. Note that after the patient placed the first tablet in his mouth there was an increase in all hormones measured. The release of TSH, which was quite large, occurred rapidly, as is seen with iv TRH, but the duration of response was much greater than that associated with iv administration (see Snyder P. J., Utiger R. D. Response to thyrotropin releasing hormone (TRH) in normal man. J. Clin Endocrinol Metab 1972; 34:380). Results obtained from the administration of the last pill, on day 5 of the study, demonstrate a significant decline in both the basal and stimulated levels of GH as well as a decline in most of the other hormone levels due either to desensitization or to depletion.

| First Tablet Time (minutes) | GH | Prl | TSH | T3 | Last Tablet Time (minutes) | GH | Prl | TSH | T3 |
| --- | --- | --- | --- | --- | --- | --- | --- | --- | --- |
| 0: | 21 | 11 | 1.6 | 152 | 0: | 10 | 7.5 | 0.6 | 180 |
| 30: | 23 | 12 | 3.4 | 150 | 30: | 11 | 6.9 | 1.0 | 177 |
| 60: | 27 | 12 | 6.6 | 142 | 60: | 14 | 7.7 | 2.2 | 168 |
| 90: | 24 | 12 | 8.4 | 139 | 90: | 13 | 8.5 | 2.6 | 192 |
| 120: | 23 | 15 | 9.7 | 168 | 120: | 14 | 9.8 | 4.8 | 188 |
| 180: | 26 | 15 | 13 | 180 | 180: | 12 | 8.1 | 7.7 | 221 |

These results suggest that plasma growth hormone in active acromegalics may be is suppressible employing heterologous desensitization administered by tablets made in accordance with the invention. In addition, these results demonstrate that the tablets are able to administer a biologically active molecule, TRH, rapidly and in significant quantity across the buccal mucosa.

The example and preferred embodiments are not intended to be limiting, and the invention applies to tablets comprised of any gel and any pharmaceutical which satisfy the criteria described herein, and the tablets may be administered in ways other than described herein.

What I claim as my invention is:

1. A method for delivering a pharmaceutical transmucosally to a human, comprising:
   providing a tablet comprising an excipient which is not readily soluble in saliva and a pharmaceutical carried by the excipient, the tablet being provided without a separate adhesive or self-adhesive and sized to fit snugly between and in contact with both a lip mucosa and an opposed gingiva mucosa so as to be held therebetween without being adhered to either mucosa, the tablet being held between the lip and the opposed gingiva mucosa by virtue of its size and the fit of the tablet between the lip and the opposed gingiva mucosa, the tablet having a structure which permits the pharmaceutical carried by the excipient to be delivered from the tablet to either or both the lip mucosa and the opposed gingiva mucosa when held therebetween; and
   placing the tablet in the mouth between the lip and gingiva mucosa and allowing it to remain there for a time sufficient to deliver a therapeutically effective amount of the pharmaceutical to the human.

2. The method according to claim 1 wherein the step of providing the tablet comprises providing a tablet sized to fit and be held between opposed mucosa in the upper lip and the upper gingiva opposed thereto, and wherein the step of placing the tablet in the mouth comprises placing it between the opposed upper lip and upper gingiva mucosa.

3. The method according to claim 1 wherein the step of providing the tablet comprises providing an elastic tablet.

4. The method according to claim 1 wherein the step of providing the tablet comprises providing a tablet comprised of an excipient which is insoluble in saliva, the method further comprising the step of removing the tablet from the mouth after a predetermined time.

5. The method according to claim 3 wherein the step of providing the tablet comprises providing a tablet in which the excipient is an elastic gel.

6. A method for delivering a pharmaceutical transmucosally to a human, comprising:
   providing a tablet comprising an excipient which is not readily soluble in saliva and a pharmaceutical carried by the excipient, which is sized to fit snugly between and in contact with both a lip mucosa and an opposed gingiva mucosa so as to be held therebetween, the tablet having a structure which permits the pharmaceutical carried by the excipient to be delivered at least bi-directionally from the tablet to either or both the lip mucosa or the opposed gingiva mucosa when held therebetween; and
   placing the tablet in the mouth between the lip and gingiva mucosa and holding it there without adhering the tablet in the mouth for a time sufficient to deliver a therapeutically effective amount of the pharmaceutical to the human.

7. A tablet for use in delivering a pharmaceutical transmucosally to a human, comprising an excipient which is not readily soluble in saliva and a pharmaceutical carried by the excipient, the tablet being sized to fit snugly between and in contact with a lip mucosa and an opposed gingiva mucosa so as to be held therebetween, the tablet having a structure which permits the pharmaceutical carried by the excipient to be delivered from the tablet to either or both the lip mucosa or the opposed gingiva mucosa when held therebetween, the tablet being sized to be held between a lip mucosa and an opposed gingiva mucosa without being adhered thereto by a separate adhesive or a self-adhesive which would otherwise adhere the tablet to the either or both the lip mucosa or the opposed gingiva mucosa, the tablet thereby being held between the lip and the opposed gingiva mucosa by virtue of its size and the fit of the tablet between the lip and the opposed gingiva mucosa.

8. The tablet according to claim 7 wherein the tablet has a size to fit and be held between opposed mucosa in the upper lip and the upper gingiva opposed thereto.

9. The tablet according to claim 7 wherein the excipient is insoluble in saliva.

10. The tablet according to claim 7 wherein the tablet is elastic.

11. The tablet according to claim 10 wherein the excipient comprises a gel.

12. The tablet according to claim 10 wherein the excipient comprises a colloidal gel.

13. The tablet according to claim 12 wherein the colloidal gel comprises water and an organic polymer selected from the group consisting of agarose, agar, agar derivatives, carrageenans, algin, furcellaran, pectins, xanthan gum and locust bean gum.

14. The tablet according to claim 12 wherein the colloidal gel comprises water and agarose.

15. The tablet according to claim 7 wherein the excipient comprises a gel and glycerol.

16. The tablet according to claim 15, wherein the gel is a colloidal gel.

17. The tablet according to claim 16 wherein the excipient comprises glycerol and the colloidal gel comprises water and an organic polymer selected from the group consisting of agarose, agar, agar derivatives, carrageenans, algin, furcellaran, pectins, xanthan gum and locust bean gum.

18. The tablet according to claim 17 wherein the colloidal gel comprises water and agarose.

19. The tablet according to claim 7 wherein the excipient comprises agarose in a concentration (w/w) with water of from about 0.1% to about 10% (excluding the pharmaceutical).

20. The tablet according to claim 19 comprising glycerol at a concentration (w/w) with water of from about 5% to about 75% (excluding the pharmaceutical).

21. A tablet for use in delivering a pharmaceutical transmucosally to a human, comprising an excipient not readily soluble in saliva and a pharmaceutical carried by the excipient, the tablet being sized to fit snugly between and in contact with a lip mucosa and an opposed gingiva mucosa and being constructed so as to be held therebetween without being adhered in the mouth, the tablet having a structure which permits the pharmaceutical carried by the excipient to be delivered from the tablet to either or both the lip mucosa or the opposed gingiva mucosa when held therebetween.

22. A tablet for use in delivering a pharmaceutical transmucosally to a human, comprising an excipient not readily soluble in saliva and not including a separate adhesive or self-adhesive, and a pharmaceutical carried by the excipient, the tablet being sized to fit snugly between and in contact with a lip mucosa and an opposed gingiva mucosa and being constructed so as to be held therebetween without being adhered to either mucosa, the excipient comprising a colloidal gel which comprises water and an organic polymer selected from the group consisting of agarose, agar, agar derivatives, carrageenans, algin, furcellaran, pectins, xanthan gum and locust bean gum, the tablet having a structure which permits the pharmaceutical carried by the excipient to be delivered from the tablet at least bi-directionally to both the lip mucosa and the opposed gingiva mucosa when held therebetween.

23. The tablet according to claim 22 wherein the excipient comprises glycerol.

24. The tablet according to claim 22 wherein the organic polymer comprises agarose in a concentration (w/w) with water of from about 0.1% to about 10% (excluding the pharmaceutical).

25. The tablet according to claim 24 comprising glycerol at a concentration (w/w) with water of from about 5% to about 75% (excluding the pharmaceutical).

26. A tablet for use in delivering a pharmaceutical transmucosally to a human, comprising an excipient not readily soluble in saliva and a pharmaceutical carried by the excipient, the tablet being sized to fit snugly between and in contact with a lip mucosa and an opposed gingiva mucosa and being constructed so as to be held therebetween without being adhered in the mouth, the excipient comprising a colloidal gel which comprises water and an organic polymer selected from the group consisting of agarose, agar, agar derivatives, carrageenans, algin, furcellaran, pectins, xanthan gum and locust bean gum, the tablet having a structure which permits the pharmaceutical carried by the excipient to be delivered from the tablet to either or both the lip mucosa and the opposed gingiva mucosa when held therebetween.

27. The tablet according to claim 26 wherein the excipient comprises glycerol.

28. The tablet according to claim 26 wherein the organic polymer comprises agarose in a concentration (w/w) with water of from about 0.1% to about 10% (excluding the pharmaceutical).

29. The tablet according to claim 28 comprising glycerol at a concentration (w/w) with water of from about 5% to about 75% (excluding the pharmaceutical).

30. The method according to claim 1 wherein the step of providing the tablet comprises providing a tablet having a structure which permits the pharmaceutical carried by the excipient to be delivered at least bi-directionally from the tablet to either or both the lip mucosa and the opposed gingiva mucosa when held therebetween.

* * * * *